United States Patent [19]
Gross et al.

[11] Patent Number: 5,686,102
[45] Date of Patent: *Nov. 11, 1997

[54] PHARMACOLOGICAL COMPOSITION FOR TOPICAL ADMINISTRATION

[75] Inventors: Udo Gross, Berlin; Joachim Röding, Wiesbaden, both of Germany; Klaus Stanzl, White Plains, N.Y.; Leonhard Zastrow, Monaco, Monaco

[73] Assignee: Lancaster Group AG, Ludwigshafen, Germany

[*] Notice: The term of this patent shall not extend beyond the expiration date of Pat. No. 5,641,509.

[21] Appl. No.: 674,851

[22] Filed: Jul. 3, 1996

Related U.S. Application Data

[63] Continuation of Ser. No. 362,504, filed as PCT/DE93/00574, May 24, 1993, abandoned.

[30] Foreign Application Priority Data

Jun. 26, 1992 [DE] Germany ............... 42 21 256.1

[51] Int. Cl.$^6$ .................. A61K 9/127; A61K 7/00
[52] U.S. Cl. ............... 424/450; 424/401; 264/4.1; 264/4.3; 514/944; 514/969
[58] Field of Search .................... 424/450, 401; 264/4.1, 4.3; 514/944, 969

[56] References Cited

U.S. PATENT DOCUMENTS

| | | | |
|---|---|---|---|
| 5,061,484 | 10/1991 | Heldebrant | 424/78 |
| 5,204,112 | 4/1993 | Hope | 424/450 |
| 5,219,538 | 6/1993 | Henderson | 428/402.2 |

FOREIGN PATENT DOCUMENTS

| | | |
|---|---|---|
| 0069307 | 1/1983 | European Pat. Off. . |
| 0 091 313 | 10/1983 | European Pat. Off. . |
| 0 105 584 | 4/1984 | European Pat. Off. . |
| 35 42 773 | 6/1987 | Germany . |
| 41 27 442 | 2/1993 | Germany . |

OTHER PUBLICATIONS

Lautenschlager in Cosmetics & Toiletries 105, May 1990.
WO 91/00110, publ. Jan. 10, 1991.
WO 89/00848, publ. Feb. 9, 1989.
WO 89/08459, publ. Sep. 21, 1989 See US 5,061,484 Above.

*Primary Examiner*—Gollamudi S. Kishore
*Attorney, Agent, or Firm*—Collard & Roe, P.C.

[57] ABSTRACT

The invention relates to pharmaceutical compositions which are incorporated into the skin with the aid of novel microaggregates as carriers. The object of the invention is to make available pharmacological active compounds in a biologically and chemically inert carrier for therapeutic and diagnostic administration to the skin or for systemic administration, and in this way to make deeper penetration into the skin or transdermal transport possible. According to the invention, this is effected by means of a pharmaceutical composition for topical administration, which contains asymmetric lamellar aggregates, consisting of phospholipids, pharmacological active compounds and fluorocarbons or fluorocarbon mixtures, the proportion of fluorocarbon being in the range from 1 to 100% weight/volume, in a pharmaceutical excipient which is suitable for topical administration. Preparation is effected by emulsification of the appropriate constituents and use in ointments, creams, lotions, pastes, gels, powders or on a dressing or plaster or by means of a spray.

21 Claims, 2 Drawing Sheets

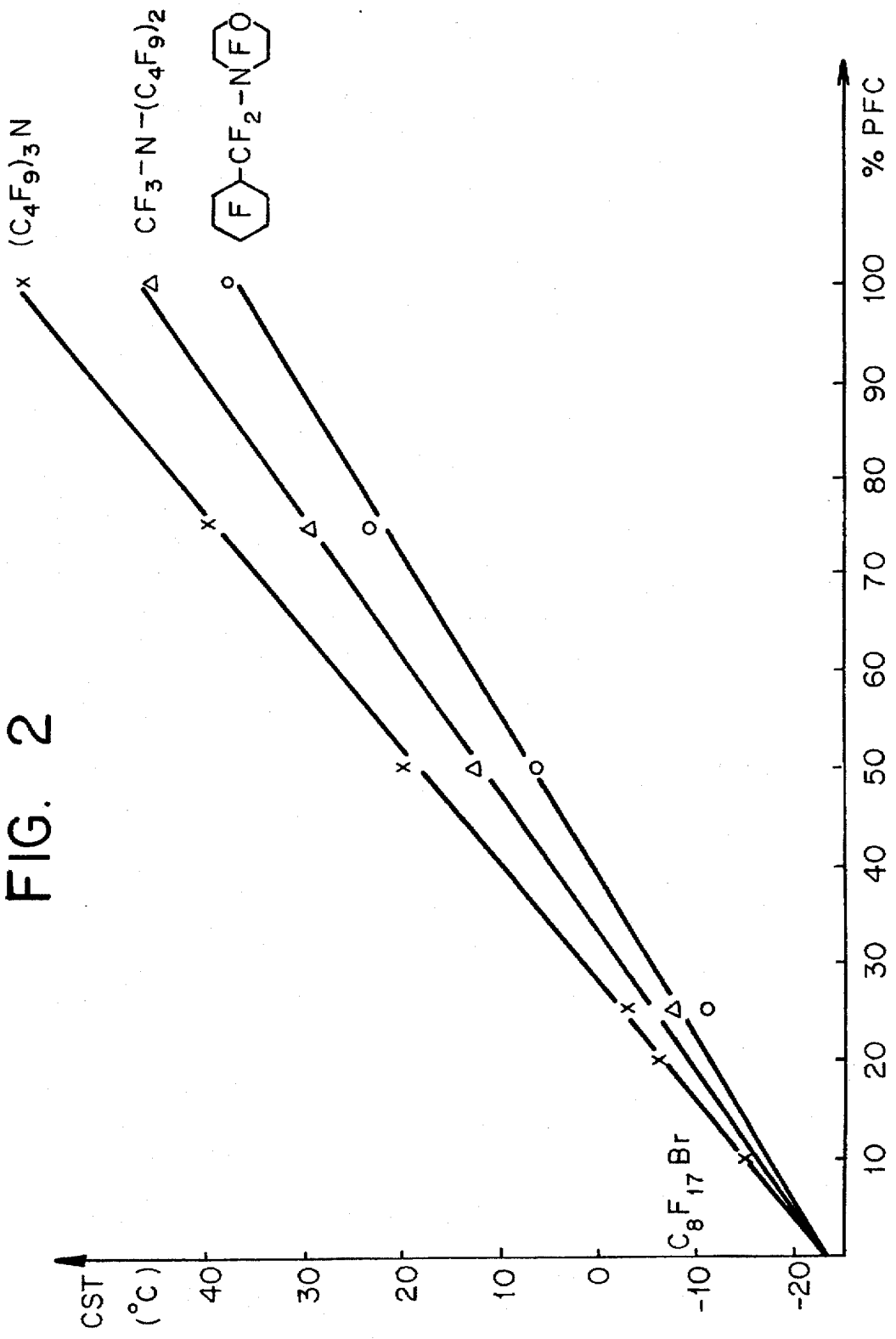

PHARMACOLOGICAL COMPOSITION FOR TOPICAL ADMINISTRATION

This is a continuation of application Ser. No. 08/362,504 filed on Dec. 22, 1994, now abandoned. International Application PCT/DE93/00574 filed on 24 Jun. 1993 and which designated the U.S.

The invention relates to pharmacological compositions based on active compounds, which can be introduced into the skin with the aid of novel microaggregates as carriers. The administration of relevant active compounds to the eye is also possible.

It is known to encapsulate pharmacological active compounds in liposomes and to apply them topically as dermatological agents. DE-A-B542773 (J. Mueller) proposes triamcinolone acetonide as a dermatological active compound. Normally, hydrophilic active compounds are included in liposomes from an aqueous solution. The inclusion of water-insoluble lipophilic active compounds, on the other hand, is not possible in this way.

It has therefore been proposed, inter alia, to use biologically inert carriers, e.g. fluorocarbons, for the transport of pharmacological active compounds. EP-A-91313 (York) proposes fluorocarbons having a vapour pressure between 1 and 16 mm Hg, which function as carriers of water-sensitive or water-insoluble compounds and are administered to the skin or to the eye. After evaporation of the fluorocarbon, the active compound remains on the skin in a metered amount. EP-A-105584 (Yuha) describes a process which, with the aid of a fluorocarbon emulsion, has a sensitising effect on the action of pharmaceuticals for the chemotherapy and radiation therapy of hypoxic cancer cells. The active compounds can be either of hydrophilic or of lipophilic nature and are administered together with or independently of the fluorocarbon emulsion. The emulsion is to be regarded as a conventional O/W emulsion, which uses emulsifiers known for emulsification.

From WO-A-89 00 848, a process for the treatment and for the administration of medicaments to the skin is known in which fluorcarbons laden with a therapeutic amount of oxygen and optionally antibiotics or other medicaments are applied to the skin in a mixture. WO-A-89 08 459 describes a perfluorcarbon emulsion containing phospholipid vesicles as a blood substitute, in which the phospholipid monomers are polymerised. In WO-A-91 00100, fluorcarbon emulsions containing phospholipids are disclosed in which the phospholipid has saturated carbon bonds.

The present invention is based on the object of making available pharmacological active compounds in a biologically and chemically inert carrier for therapeutic and diagnostic administration to the skin or to the eye or for systemic administration and in this way to ensure a deeper penetration into the skin or to ensure transdermal transport.

According to the invention, a pharmaceutical composition for topical administration consists of a fluorocarbon-containing lamellar phospholipid aggregate as the carrier for pharmacological active compounds, the amount of fluorocarbon or fluorocarbon mixture being in the range from 1 to 100% weight/volume and the phospholipid has a phosphatidylcholine content of 30 to 99% by weight.

Surprisingly, an interaction takes place between the fluorocarbon, the active compound and the phospholipid to give an asymmetric lamellar aggregate with particular properties with respect to the dermal system. Unlike the known aqueous liposomes (vesicles), these novel aggregates carry in their core hydrophobic fluorocarbons and thus form monolayers having an inverse arrangement, to which is optionally attached a structure of bilayer films. According to the invention, unlike the known symmetric vesicles, the lamellar aggregates therefore have an asymmetric structure. Because of this peculiarity of their structural arrangement, the novel aggregates are designated asymmetric lamellar carriers. Their exceptional colloid chemical stability can be traced back to the lamellar structure and to the surface charge of the aggregates. The latter can be traced back to the choice of suitable phospholipids or mixtures thereof of natural as well as of synthetic origin. Electrically charged phospholipids such as phosphatidylethanolamine (PE), N-acyl-PE, N-acetyl-PS or phosphatidic acid (PA) in addition to phosphatidylcholine in the concentration range from 30 to 99% are primarily responsible for an advantageous action in this sense.

The fluorocarbon is located in the core of these aggregates as a lipophilic substance. The lamellar structure and its asymmetric arrangement were detected by $^{31}$P-NMR and in particular by special electron-microscopic investigations. The particle sizes and distributions were determined by QLS investigations. These vary between particle diameters of 50 and 1000 nm. The particle sizes are dependent on the energy intensity of the homogenisation process.

A plurality of fluorocarbons can be employed, e.g. aliphatic straight-chain and branched fluoroalkanes, mono- or bicyclic and optionally fluoroalkyl-substituted fluorocycloalkanes, perfluorinated aliphatic or bicyclic amines, bis(perfluoroalkyl)ethenes or mixtures thereof. Particularly preferred fluorocarbons are those such as perfluorodecalin, F-butyltetrahydrofuran, perfluorotributylamine, perfluorooctyl bromide, bis-fluoro (butyl)ethene or bis-fluoro(hexyl)ethene or $C_6$-$C_9$-perfluoroalkanes.

The amount of fluorocarbons here is in the range from 1 to 100% w/v, preferably in the range from 40 to 100%. A particularly preferred range is that from 70 to 100% w/v.

According to the invention, the phospholipids employed are natural phospholipids such as soya lecithin and egg lecithin, synthetic phospholipids and/or partially hydrogenated phospholipids, the content of phosphatidylcholine in these phospholipids being in the range from 30 to 99% by weight, in particular 70 to 90% by weight, i.e. in most cases an enrichment of phosphatidylcholine takes place in the phospholipids.

In addition to phosphatidylcholine, lysolecithins can also be present in the concentration range from 0.1 to 5% by weight.

The claimed action of the phospholipids is verified by appropriate negative zeta potentials and by the measurement of charge densities (on titration with a cationic polyelectrolyte).

By means of separate investigations, it was possible to determine the dependence of the penetration rates and the depth of penetration on the particle size of the aggregates experimentally in animal experiments using labelled encapsulated fluorocarbons. According to these experiments, smaller particles migrate more rapidly and deeply into the skin tissue than larger particles. The choice of fluorocarbons or mixtures thereof according to their lipid solubility (represented by their critical solubility temperature CST in n-hexane) permits, as a further important criterion, the control of the residence time in the tissue. While, e.g. perfluorotributylamine (F-TBA, CST 59° C.) with a high CST value and poor lipid solubility has a relatively large residence time, in contrast to this perfluorodecalin (PFD, CST 22° C.), but also F-butyltetrahydrofuran, F-hexane and others are released correspondingly more rapidly from the tissue. With the aid of fluorocarbon mixtures, in this way systems having desired CST values, i.e. lipid and membrane solubilities, with respect to the intended use can be prepared in a controlled manner.

The content of the fluorocarbons as oxygen carriers in the lamellar aggregates can vary between 1 and 100% w/v according to the intended application. The following are particularly suitable as fluorocarbons: aliphatic straight-chain and branched alkanes having 6 to 12 carbon atoms, e.g. perfluorohexane, perfluorooctane, perfluorononane;

mono- or bicyclic alkanes, which are optionally F-alkyl-substituted, e.g. perfluoromethylcyclohexane, perfluorodecalin;

aliphatic tertiary amines, N-containing polycycles, e.g. perfluorotripropylamtne, perfluorotributylamine, F-cyclohexylmethylmorpholine;

perfluoroethers, such as aliphatic ethers, F-alkylfurans, bicyclic and substituted bicyclic ethers having 2 or 3 oxygen atoms in the molecule, e.g. perfluorodihexyl ethers, perfluorobutyltetrahydrofuran, perfluoropolyethers;

perfluoroalkyl halides, e.g. perfluorooctyl bromide, perfluorohexyl bromide, perfluorooctyl chloride;

bis-F(alkyl)ethenes, e.g. bis-F(butyl)ethene, bis-F(hexyl) ethene.

The term "fluorocarbons" used here is understood as meaning perfluorinated or highly fluorinated carbon compounds or mixtures which are able to transport gases such as $O_2$ and $CO_2$. Highly fluorinated hydrocarbon compounds within the meaning of this invention are those in which most of the hydrogen atoms are replaced by fluorine atoms, e.g. the bis-F(alkyl)ethenes which, as far as can be detected, are chemically and biologically inert and thus non-toxic. This is usually achieved if approximately up to 90% of the hydrogen atoms are replaced by fluorine atoms. Preferred fluorocarbons within the meaning of the present invention are those in which at least 95% of the hydrogen atoms are replaced, more preferably 98% and most preferably 100%.

Individual fluorine atoms can also be replaced by other halogen atoms such as bromine or chlorine.

Possible phospholipids are naturally occurring phospholipids such as soya or egg lecithin, and also lecithins which can be prepared synthetically (phospholipids), which overall are known as skin-compatible and good for the skin. Because of the advantageous action on the stability of the asymmetric lamellar aggregates, phospholipid mixtures containing an amount from 30 to 99% by weight of phosphatidylcholine in addition to other naturally occurring accompanying products are preferably used. The phospholipid content in the cosmetic formulation varies between 0.5 and 20%.

The novel lamellar phospholipid aggregates have the advantageous property after topical administration of getting through the horny layer and making the pharmaceutical active compound available: in the epidermal and dermal region and also in the adjoining tissue or of supplying it to the vessel for systemic absorption. These penetration properties are utilised according to the invention to transport pharmaceuticals into the skin tissue in interaction with the fluorocarbon and the phospholipid and there or in another site to achieve a desired therapeutic or diagnostic effect. This takes place in contrast to the invention descriptions mentioned in the prior art, which do not permit the transport of the fluorocarbons into deeper-lying regions of the skin. The known processes are ineffective in respect of the claimed effect.

The pharmaceutical composition according to the invention contains as pharmacological active compounds particularly those of the following group:

dermatological active compounds, for example virustatics or virucidal pharmaceuticals, antimycotics, heparins (e.g. heparin calcium, heparin sodium, low molecular weight heparins), antibiotics, corticoids, antiinfectious agents, acne active compounds, local anaesthetics, antiinflammatories, antihistamines or antipsoriatic agents;

systemic active compounds, for example non-steroidal analgesics/antirheumatics (e.g. diclofenac sodium, diclofenac diethylamine salt, etofenamate, flufenamic acid, 2-hydroxyethyl salicylate, ibuprofen, indomethacin, piroxicam), opiate receptor agonists and antagonists (e.g. buprenorphine, fentanyl, pentazocine, pethidine, tilidine, tramadol, naloxone), histamine antagonists (e.g. bamipine lactate, chlorphenoxamine HCl, clemastine hydrogenfumarate, dimetindene maleate, pheniramine hydrogenmaleate), insulins, regulatory peptides and their inhibitors (e.g. anterior pituitary hormones and their inhibitors, posterior pituitary hormones, hypothalamus hormones), sedatives/hypnotics (e.g. diazepam);

active compounds from the group consisting of cytostatics, cancerostatics, immunomodulators and vaccines.

A preferred dermatological active compound is, for example, rosmarinic acid or another virucidal or virustatic active compound occurring in plants. A preferred systemic active compound is, for example, a low molecular weight or high molecular weight heparin, an oligopeptide or a polypeptide. Other preferred active compounds are vitamins (E, A, B, C), muramyl peptides, doxorubicin, gentamycin, gramicidin, dexamethasone, hydrocortisone, progesterone, prednisolone or derivatives derived therefrom and/or acid or base addition salts.

Using relevant active compounds and active compound combinations, an antineoplastic therapy, an antimicrobial and antiviral therapy and other types of therapy are possible with appropriate indications.

In general, the amounts of active compound from the therapeutic point of view are very low, so that, e.g. in the case of soluble active compounds solubilities of 0.5 to 12 g/100 ml of fluorocarbon are sufficient for medicinal administration. If these solubilities are not provided, then emulsification by means of the still incompletely clarified interaction of fluorocarbon and phospholipid using known processes is also possible in order to obtain the appropriate pharmaceutical composition. The active compounds can therefore be incorporated into the novel carrier in the amount which is sufficient from the present medical point of view.

The invention also relates to a process for the preparation of a phospholipid-containing pharmaceutical composition, which consists in emulsifying phospholipids having a content of phosphatidylcholine of 30 to 99% by weight with a fluorocarbon or fluorocarbon mixture, a pharmacological active compound or an active compound combination being incorporated into the emulsion, and the amount of fluorocarbon being in the range from 1 to 100% weight/volume, and the asymmetric lamellar aggregates obtained in this way being incorporated into an excipient suitable for topical administration as active compound carriers having a particle size from 50 to 1000 nm.

A water-soluble lipophilic active compound or an active compound combination is particularly preferred here which dissolves in the fluorocarbon or is dispersed/suspended therein. Fluorocarbons are basically very hydrophobic organic liquids. The broad spectrum of the chemical molecule structures enables, however, a gradation of the lipophilic properties, i.e. the different solubility properties of the active compounds can then be adapted in the individual case to a selected fluorocarbon.

In the present preparation process, the often complicated and sensitive molecular structure of the active compounds with different binding stabilities must be considered. This must be particularly taken into account both in the loading of the fluorocarbons or fluorocarbon mixtures, in the interaction with the phospholipids and in the homogenisation process, since as a result of the homogenisation an external energy input takes place, using which the lamellar phospholipid aggregates are produced. This energy input must be proportioned such that the molecular structure of the pharmaceuticals is retained. The homogenisation can be effected by mechanical mixers, ultrasonic mixers, pressure homogenisers, etc. and is to be adapted to the particular pharmaceutical by the person skilled in the art. Since fluorocarbons at the same time serve as oxygen carriers, the use of antioxidants to avoid autoxidation processes can be reported.

BRIEF DESCRIPTION OF THE DRAWINGS

The invention will be illustrated in greater detail below by means of examples. In the accompanying drawings FIG. 2 is a diagram of the critical solubility temperatures of perfluorocarbon mixtures in n-hexane using F-octylbromide as a starting point.

Figure 1:
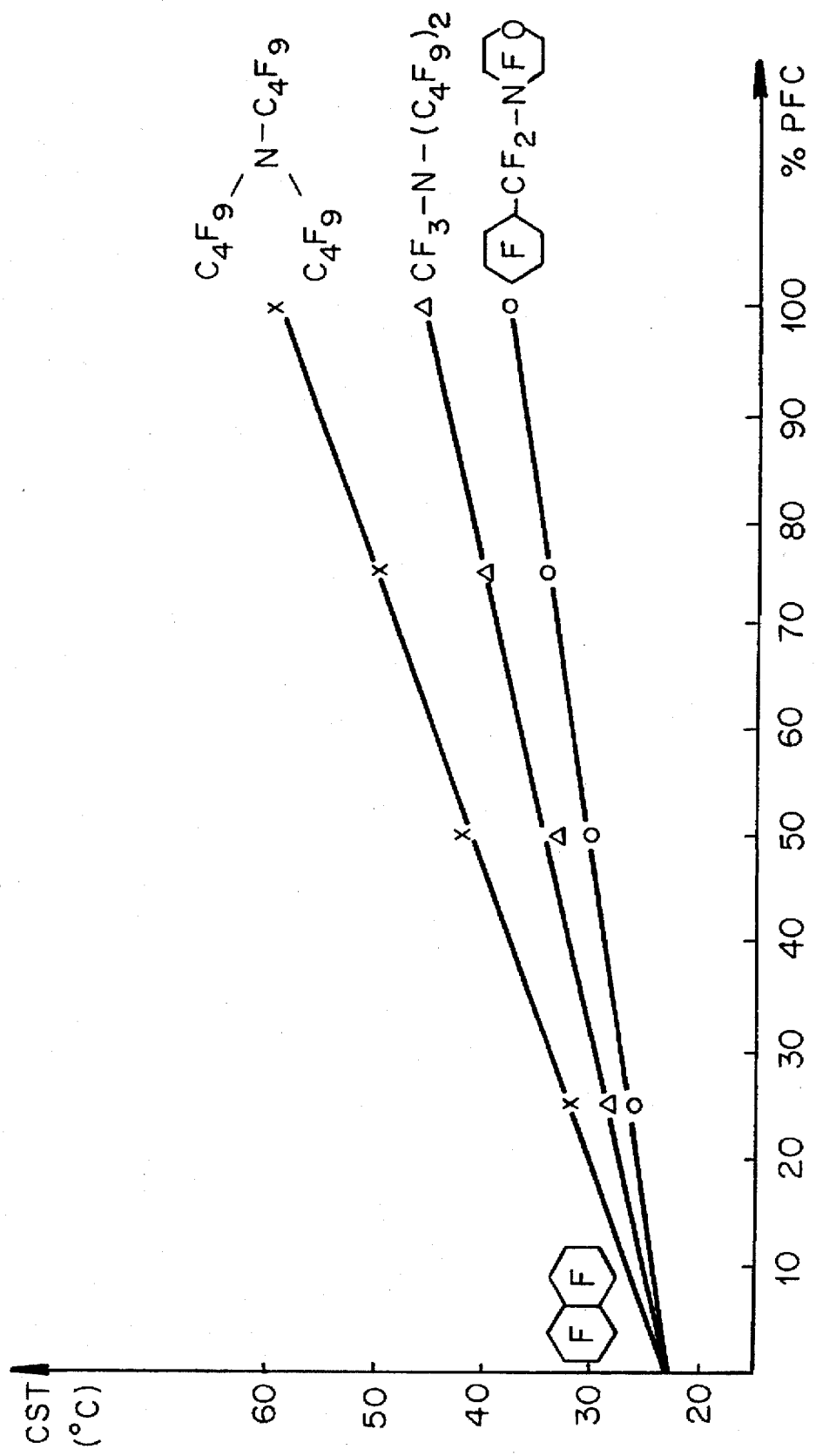
FIG. 1 is a diagram of the critical solubility temperatures (CST) of perfluorocarbon mixtures in n-hexane using perfluorodecalin as a starting point

Some selected fluorocarbons and their $O_2$ solubility, their vapour pressure and the critical solubility temperature are shown in Table 1. Starting from these values, the desired characteristics for mixtures of fluorocarbons can be selected for penetration into the skin with the aid of the composition according to the invention.

TABLE 1

| Fluorocarbon | $O_2$ solubility [ml of $O_2$/100 ml of Fc] | Vapour Pressure $R_{37°\,C.}$ [mm Hg] | CST [°C.] |
| --- | --- | --- | --- |
| Perfluorooctyl bromide | 50 | 14 | −24.5 |
| Perfluorodecalin | 40 | 12.5 | 22 |
| Bis-F(butyl)ethene | 50 | 12.6 | 22.5 |
| F-cyclohexylmethyl-morpholine | 42 | 4 | 38.5 |
| F-tripropylamine | 45 | 18.5 | 43 |
| F-dihexyl ether | 45 | 2 | 59 |
| F-tributylamine | 40 | 1 | 59 |
| Perfluorodecalin-F-tributylamine 1:1 | 40 | 7 | 42 |
| Perfluorobutyl-tetrahydrofuran | 52 | 51 | 29 |
| F-methylcyclohexane | 57 | 180 | 8.2 |
| F-hexane | 58 | 414 | 20 |

Example 1

A 10% strength aqueous phospholipid solution of soya lecithin and with 40% phosphatidylcholine was mixed together with a fluorocarbon mixture of perfluorodecalin (90%) and F-dibutylmethylamine (10%) and a pharamacological active compound in an ultrasonic disintegrator with cooling. The asymmetric lamellar phospholipid aggregates obtained in this way had a mean particle size of about 240 nm and contained the pharmacological active compound in interaction with the fluorocarbon mixture.

Example 2 Gel

The product obtained in Example 1 was mixed with the individual constituents, the customary procedures for pharmaceutical processes being employed. The following proportions resulted in this case for the finished pharmaceutical preparation

| | |
| --- | --- |
| Asymmetric lamellar phospholipid aggregates | 30% |
| Diazepam | 2% |
| Polyacrylic acid | 1% |
| TEA | 1% |
| Preservative | 0.8% |
| Distd. water | to 100% |

Example 3 Alcoholic Solutions

The procedure was as in Example 2, the following constituents being added

| | |
| --- | --- |
| Asymmetric lamellar phospholipid aggregates | 20% |
| Ethanol | 16% |
| Heparin Na | 150,000 IU |
| Distd. water | to 100% |

Example 4 Cream

The procedure was as in Example 2, the following constituents being added

| | |
| --- | --- |
| Asymmetric lamellar phospholipid aggregates | 20% |
| Clotrimazole | 1% |
| White petroleum jelly | 79% |

Example 5 Lotion

The procedure was as in Example 2, the following constituents being added

| | |
| --- | --- |
| Asymmetric lamellar phospholipid aggregates | 20% |
| Estradiol | 0.5% |
| Polyacrylic acid | 0.2% |
| TEA | 0.2% |
| HCOH (37%) | 0.2% |
| Distd. water | to 100% |

We claim:

1. Pharmaceutical composition for topical administration, comprising asymmetric lamellar aggregates, comprising phospholipids having a phosphatidylcholine content of 30% to 99% by weight, pharmacological active compounds and fluorocarbon, the amount of fluorocarbon being in the range from 1% to 100% weight/volume, in a pharmaceutical excipient suitable for topical administration; and said asymmetric lamellar phospholipid aggregates comprising a central core of fluorocarbons surrounded by at least three layers of phospholipid molecules wherein the layer adjacent to said central core has the lipophilic moiety of the phospholipid interact with the fluorocarbon.

2. Composition according to claim 1, wherein the lamellar aggregates have an asymmetric 3-layer structure originating from their fluorocarbon core.

3. Composition according to claim 1, wherein the fluorocarbon is selected from the group consisting of aliphatic straight-chain fluoroalkanes, aliphatic branched fluoroalkanes, monocyclic fluorocycloalkanes, monocyclic fluoroalkyl-substituted fluorocycloalkanes, bicyclic fluorocycloalkanes, bicyclic fluoroalkylsubstituted fluorocycloalkanes, perfluorinated aliphatic amines, perfluoroinated bicyclic amines, bis(perfluoroalkyl) ethenes, and mixtures thereof.

4. Composition according to claim 3, wherein the fluorocarbon is selected from the group consisting of perfluorodecalin, F-butyltetrahydrofuran, perfluorotributylamine, perfluorooctyl bromide, bis-fluoro(butyl)ethene and $C_6$-$C_9$-perfluoroalkanes.

5. Composition according to claim 1, wherein the amount of fluorocarbon is in the range from 20% to 100% weight/volume.

6. Composition according to claim 1, wherein the amount of fluorocarbon is in the range from 40% to 100% weight/volume.

7. Composition according to claim 1, wherein the amount of fluorocarbon is in the range from 70% to 100% weight/volume.

8. Composition according to claim 1, wherein the phospholipids are selected from the group consisting of natural phospholipids, synthetic phospholipids, and the mixtures thereof in a concentration between 0.5% and 20%.

9. Composition according to claim 1, wherein phosphatidylcholine is present in an amount from 70% to 90% by weight.

10. Composition according to claim 1, wherein the lipid fraction used, in addition to phosphatidylcholine, lysolecithins are present in the concentration range from 1% to 5% by weight.

11. Composition according to claim 1, wherein there is a pharmocological active compound selected from the group consisting of dermatological active compounds, systemic active compounds, and mixtures thereof.

12. Composition according to claim 11, wherein the pharmacological active compound is a pharmaceutical selected from the group consisting of virustatics, virucidal pharmaceuticals, antimycotics, heparins, antibiotics, corticoids, antiinfectious agents, anti-acne compounds, local anesthetics, antiinflammatories, antihistamines, antipsoriatic agents, and the mixtures thereof.

13. Composition according to claim 11, wherein the systemic active compound is a pharmaceutical selected from the group consisting of the non-steroidal analgesics, antirheumatics, opiate receptor agonists, opiate receptor antagonists, heparins, histamine antagonists, insulins, regulatory peptides, sedative and hypnotics.

14. Composition according to claim 11, wherein the dermatological active compound is a virucidal active compound.

15. Composition according to claim 13, wherein the systemic active compound is a low molecular weight heparin, a high molecular weight heparin, an oligopeptide or a polypeptide.

16. Process for the preparation of a phospholipid-containing pharmaceutical composition comprising the steps of emulsifying phospholipids having a phosphatidylcholine content of 30% to 99% by weight with a fluorocarbon or fluorocarbon mixture, a pharmacological active compound or an active compound combination being incorporated into the emulsion, and the amount of fluorocarbon being in the range from 1 to 100 per cent weight/volume to produce asymmetric lamellar aggregates; and incorporating the asymmetric lamellar aggregates obtained in this way into an excipient suitable for topical administration as active compound carriers having a particle size from 50 nm to 1000 nm; and said asymmetric lamellar phospholipid aggregates comprising a central core of fluorocarbons surrounded by at least three layers of phospholipid molecules wherein the layer adjacent to said central core has the lipophilic moiety of the phospholipid interact with the fluorocarbon.

17. Process according to claim 16, wherein the amount of fluorocarbon is in the range from 20% to 100% by weight/volume; and the amount of phosphatidylcholine in the phospholipid is in the range from 70% to 90% by weight.

18. Process according to claim 16, wherein the amount of fluorocarbon is in the range from 40% to 100% by weight/volume.

19. In a method for the topical application of a pharmaceutical composition, the improvement comprising topically applying a system containing phospholipids having a phosphatidylcholine content of 30% to 99% by weight, pharmacological active compounds and fluorocarbons in the form of asymmetric lamellar aggregates;

the fluorocarbon content being in the range from 0.2% to 100% weight/volume; and the system being present for topical administration in a carrier selected from the group consisting of ointment, cream, lotion, paste, gel, powder a dressing, a plaster, and a spray; and said asymmetric lamellar phospholipid aggregates comprising a central core of fluorocarbons surrounded by at least three layers of phospholipid molecules wherein the layer adjacent to said central core has the lipophilic moiety of the phospholipid interact with the fluorocarbon.

20. Composition according to claim 11, wherein there is a pharmaceutical active compound selected from the group consisting of a cytostatic, a cancerostatic, an immunodulator, a vaccine, and mixtures thereof.

21. Composition according to claim 14, wherein the dermatological active compound is rosmarinic acid.

* * * * *

UNITED STATES PATENT AND TRADEMARK OFFICE
CERTIFICATE OF CORRECTION

PATENT NO.   :   5,686,102
DATED        :   November 11, 1997
INVENTOR(S)  :   GROSS ET AL It is certified that error appears in the above-indentified patent and that said Letters Patent is hereby corrected as shown below:

In the Title page, column 1, line [63], change "May" to --June--.

Signed and Sealed this

Tenth Day of February, 1998

Attest:

BRUCE LEHMAN

Attesting Officer

Commissioner of Patents and Trademarks